US00PP16343P2

(12) United States Plant Patent
Sakazaki

(10) Patent No.: US PP16,343 P2
(45) Date of Patent: Mar. 14, 2006

(54) ***CALIBRACHOA* PLANT NAMED 'USCALI100'**

(50) Latin Name: ***Calibrachoa* sp.**
Varietal Denomination: USCALI100

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 21 days.

(21) Appl. No.: 11/045,979

(22) Filed: Jan. 28, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A distinct cultivar of *Calibrachoa* plant named 'USCALI100', characterized by its semi-upright to cascading plant habit; freely branching habit; freely flowering habit; relatively large dark violet-colored flowers with prominent dark purple-colored venation; good weather tolerance; and resistance to *Thielaviopsis*.

1 Drawing Sheet

Botanical designation: *Calibrachoa* sp.
Cultivar denomination: 'USCALI100'.

BACKGROUND OF THE INVENTION

The present Invention relates to a new and distinct cultivar of *Calibrachoa* plant, botanically known as *Calibrachoa* sp., and hereinafter referred to by the cultivar name 'USCALI100'.

The new *Calibrachoa* is a product of a planned breeding program conducted by the Inventor in Hikone, Shiga, Japan. The objective of the program is to create new heat-tolerant and disease-resistant *Calibrachoa* cultivars with semi-upright plant habit and attractive flower colors.

The new *Calibrachoa* originated from a cross-pollination made by the Inventor on Apr. 12, 2000 of a proprietary seedling selection of *Calibrachoa* identified as code number C50-2, not patented, as the female, or seed, parent with a proprietary seedling selection of *Calibrachoa* identified as code number K-1, not patented, as the male, or pollen, parent. The new *Calibrachoa* was selected by the Inventor on Jun. 24, 2001 in a controlled environment in Gensingen, Germany.

Asexual reproduction of the new cultivar by terminal cuttings taken in a controlled environment in Gensingen, Germany since Jun. 25, 2001, has shown that the unique features of this new *Calibrachoa* are stable and reproduced true to type in successive generations.

SUMMARY OF THE INVENTION

Plants of the cultivar USCALI100 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USCALI100'. These characteristics in combination distinguish 'USCALI100' as a new and distinct cultivar of *Calibrachoa:*

1. Semi-upright to cascading plant habit.
2. Freely branching habit.
3. Freely flowering habit.
4. Relatively large dark violet-colored flowers with prominent dark purple-colored venation.
5. Good weather tolerance; tolerant to rain and low and high temperatures.
6. Resistant to *Thielaviopsis*.

Plants of the new *Calibrachoa* differ primarily from plants of the female parent selection primarily in flower color as plants of the female parent selection have violet blue-colored flowers. Plants of the new *Calibrachoa* differ primarily from plants of the male parent selection primarily in growth habit as plants of the male parent selection are more creeping than plants of the new *Calibrachoa*.

Plants of the new *Calibrachoa* can be compared to plants of the cultivar Colorburst Blue, not patented. In side-by-side comparisons conducted in Gensingen, Germany, plants of the new *Calibrachoa* had a more upright plant habit and larger flowers than plants of the cultivar Colorburst Blue.

Plants of the new *Calibrachoa* can be compared to plants of the cultivar Sunbelkubu, not patented. In side-by-side comparisons conducted in Gensingen, Germany, plants of the new *Calibrachoa* had a more upright plant habit and larger flowers than plants of the cultivar Sunbelkubu.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Calibrachoa*.

The photograph at the top of the sheet is a close-up view of typical flowers and leaves of 'USCALI100'.

The photograph at the bottom of the sheet comprises a side perspective view of a typical plant of 'USCALI100' grown in a container.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers were used for the aforementioned photographs and following description. Plants were about 12 weeks from planting rooted cuttings. Plants were grown under conditions which closely approximate commercial production conditions during the summer in Bonsall, Calif. in an outdoor nursery. During the production period, day temperatures ranged from 18 to 35° C. and night temperatures ranged from 10 to 21° C.

Botanical classification: *Calibrachoa* sp. cultivar USCALI100.

Parentage:

*Female, or seed, parent.*—Proprietary seedling selection of *Calibrachoa* sp. identified as code number C50-2, not patented.

*Male, or pollen, parent.*—Proprietary seedling selection of *Calibrachoa* sp. identified as code number K-1, not patented.

Propagation:

*Type cutting.*—Terminal vegetative cuttings.

*Time to initiate and develop roots.*—Summer: About three weeks at 20° C. Winter: Abour four weeks at 20° C.

*Root description.*—Fine, freely-branching; whitish in color.

Plant description:

*Form.*—Annual flowering plant; initially upright to semi-upright, eventually cascading; uniformly mounded appearance.

*Usage.*—Appropriate for hanging baskets, window boxes and patio containers.

*Plant height* (*from soil level to top of plant plane*).—About 15 cm.

*Plant diameter.*—About 48 cm.

*Growth rate.*—Moderate to rapid growth rate; vigorous.

*Branching habit.*—Freely branching, about eight primary branches per plant each with about four or five secondary branches; pinching is typically not required.

*Lateral branch description.*—Length: About 27 cm. Diameter: About 2.5 mm. Internode length: About 1.6 cm. Texture: Pubescent. Color: 144B.

*Foliage description.*—Arrangement: Alternate until flowering, then opposite; simple. Length: About 2.2 cm. Width: About 1 cm. Shape: Obovate. Apex: Broadly acute to rounded. Base: Attenuate. Margin: Entire. Texture, upper surface: Slightly pubescent. Texture, lower surface: Slightly glandular; pubescent. Venation pattern: Pinnate; arcuate. Color: Developing foliage, upper surface: 146A. Developing foliage, lower surface: 146B. Fully expanded foliage, upper and lower surfaces: 146B. Venation, upper surface: 144C. Venation, lower surface: 144D. Petiole: Length: About 6 mm. Diameter: About 1.5 mm. Texture, upper and lower surfaces: Smooth. Color, upper surface: 144C. Color, lower surface: 144D.

Flower description:

*Flower type and habit.*—Flowers face upright or outward; single, relatively large, axillary; salverform. Flowers persistent. Freely flowering habit, about 64 flowers and flower buds per lateral stem. Flowers not fragrant. Flowers face outward and bending upwardly.

*Natural flowering season.*—April through September in Southern California; flowering continuous during this period.

*Time to flower.*—Early flowering; plants begin flowering about four to six weeks after planting.

*Flower longevity on the plant.*—About seven to ten days.

*Flower size.*—Diameter: About 3 cm. Depth: About 2.6 cm. Tube length: About 1.7 cm. Flower throat diameter: About 6 mm by 8 mm. Flower tube diameter: About 2.5 mm.

*Flower buds.*—Length: About 2.2 cm. Diameter: About 4 mm. Shape: Elongated oblong. Color: 201D.

*Corolla.*—Arrangement/appearance: Single whorl of five petals, fused into flared trumpet. Petal length from throat: About 1 cm. Petal width: About 1.5 cm. Petal shape: Roughly cordate to fan-shaped. Petal apex: Cordate. Petal margin: Entire. Petal texture, upper and lower surfaces: Smooth, glabrous; velvety. Throat texture: Smooth. Tube texture: Pubescent. Color: Petal, when opening, upper surface: Brighter and more red than 83A. Petal, when opening, lower surface: More gray than 84C. Petal, opened flower, upper surface: 83A; prominent venation, 79B; ground color becoming coming closer to 77A with development. Petal, opened flower, lower surface: 79D; venation, 79B. Flower throat (inside): 148D; venation, 79B. Flower tube (outside): 148D; venation, 79B.

*Sepals.*—Arrangement/appearance: Single whorl of five sepals, fused at base; star-shaped. Length: About 6 mm. Width: About 3 mm. Shape: Narrowly elliptic. Apex: Acute. Margin: Entire. Texture, upper and lower surfaces: Pubescent. Color, upper surface: 146A. Color, lower surface: 146B.

*Peduncles.*—Length: About 1.2 cm. Width: About 1 mm. Strength: Moderately strong. Angle: About 45° from vertical. Texture: Pubescent. Color: 144A.

*Reproductive organs.*—Stamens: Quantity: Five per flower. Anther shape: Oval. Anther length: Less than 1 mm. Anther color: 11A. Pollen amount: Scarce. Pollen color: 12A. Pistils: Quantity: One per flower. Pistil length: About 1 cm. Stigma shape: Rounded. Stigma color: 145A. Style length: About 7 mm. Style color: 145D. Ovary color: 145B.

*Seed/fruit.*—Seed and fruit production has not been observed.

Disease/pest resistance: Plants of the new *Calibrachoa* have been noted to be resistant to *Thielaviopsis*. Plants of the new *Calibrachoa* have not been noted to be resistant to other pathogens and pests common to *Calibrachoas*.

Weather/temperature tolerance: Plants of the new *Calibrachoa* are tolerant to rain and wind and have been observed to tolerate temperatures from 1 to 41° C.

It is claimed:

1. A new and distinct cultivar of *Calibrachoa* plant named 'USCALI100', as illustrated and described.

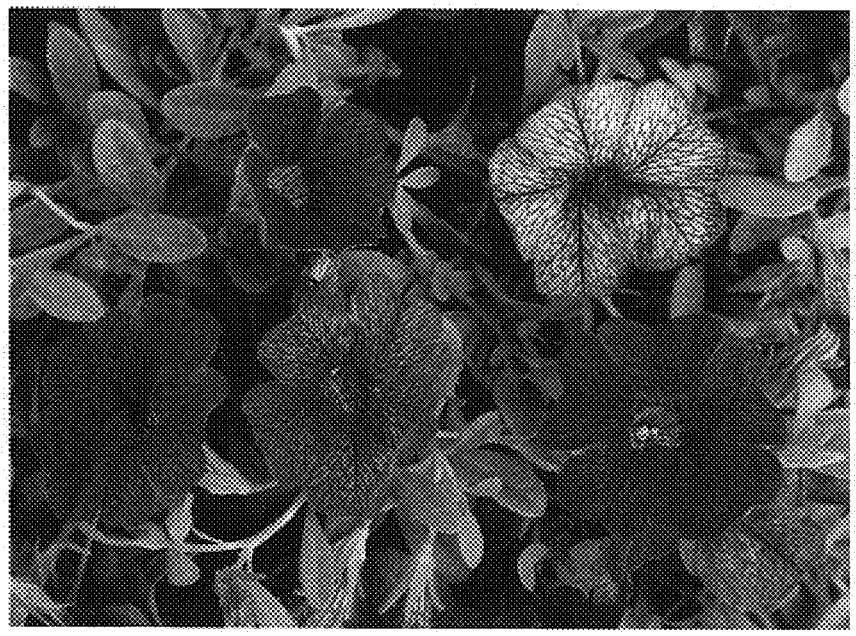
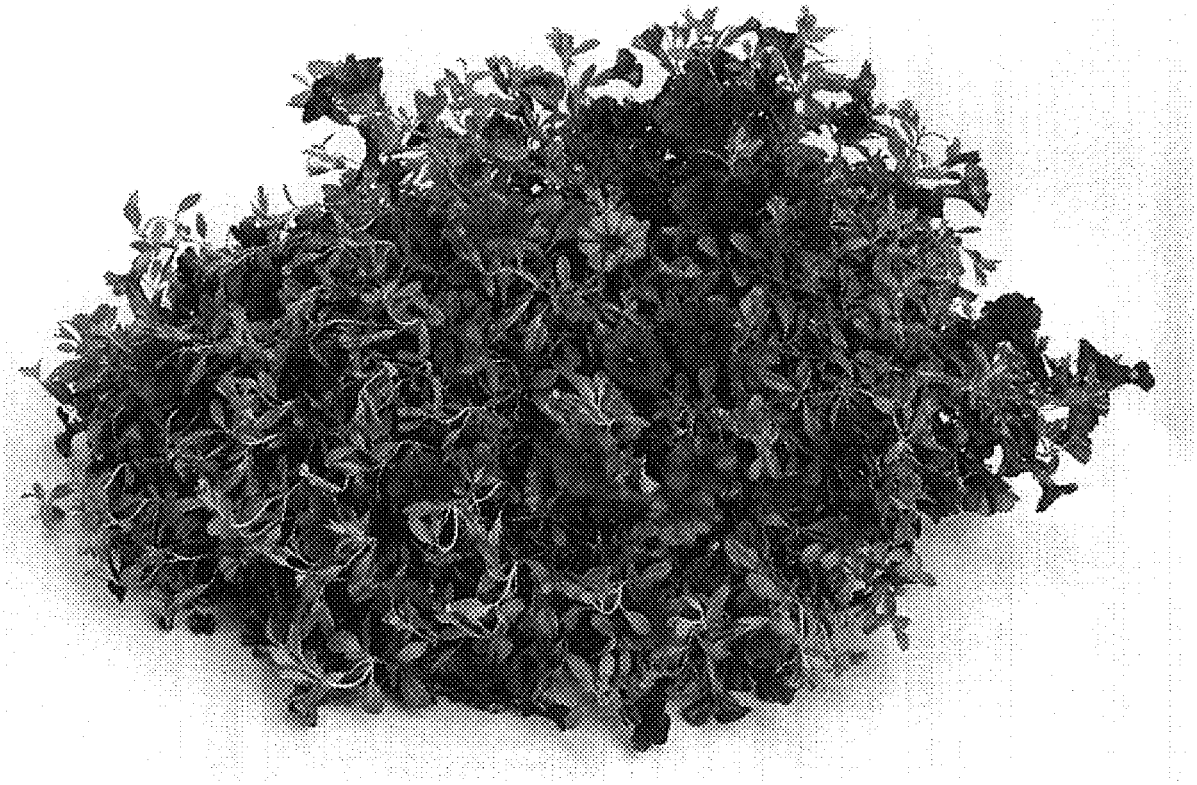

* * * * *